United States Patent [19]

Ditlow et al.

[11] Patent Number: 5,202,267
[45] Date of Patent: Apr. 13, 1993

[54] SOL CAPTURE IMMUNOASSAY KIT AND PROCEDURE

[75] Inventors: Charles C. Ditlow, Brockton; L. Edward Cannon, Wayland; Francis X. Cole, Stow; Gene A. Davis, Lexington; Eric C. Sigillo, Meuthen; Alicia G. Danti, Billerica, all of Mass.

[73] Assignee: Hygeia Sciences, Inc., Newton, Mass.

[21] Appl. No.: 177,114

[22] Filed: Apr. 4, 1988

[51] Int. Cl.$^5$ .................................................. G01N 33/553
[52] U.S. Cl. .................................... 436/525; 422/58; 422/61; 422/101; 436/518; 436/523; 436/824; 436/825
[58] Field of Search ................ 222/189, 420; 436/518, 436/523, 525, 818, 825, 824; 422/58, 61, 101

[56] References Cited

U.S. PATENT DOCUMENTS

| | | | |
|---|---|---|---|
| 3,088,875 | 5/1963 | Fisk | 167/84.5 |
| 3,096,250 | 7/1963 | Ingraham | 167/84.5 |
| 3,189,223 | 6/1965 | Mackal | 222/1 |
| 3,652,761 | 3/1972 | Weetall | 424/12 |
| 3,826,613 | 7/1974 | Parikh et al. | 23/230 |
| 3,862,030 | 1/1975 | Goldberg | 210/24 |
| 3,873,682 | 3/1975 | Ogawa | 424/12 |
| 3,960,491 | 6/1976 | Giaever | 23/230 |
| 3,970,518 | 7/1976 | Giaever | 195/1.5 |
| 4,014,653 | 3/1977 | Gianos et al. | 23/259 |
| 4,018,886 | 4/1977 | Giaever | 424/12 |
| 4,070,246 | 1/1978 | Kennedy et al. | 195/99 |
| 4,092,116 | 5/1978 | Giaever | 23/230 |
| 4,115,535 | 9/1978 | Giaever | 424/1 |
| 4,118,192 | 10/1978 | Sawai et al. | 424/12 |
| 4,123,509 | 10/1978 | Banik et al. | 424/12 |
| 4,138,214 | 2/1979 | Givner | 23/230 |
| 4,169,138 | 9/1979 | Jonsson | 424/12 |
| 4,184,849 | 1/1980 | Cambiaso et al. | 23/230 |
| 4,203,724 | 5/1980 | Sawai et al. | 23/230 |
| 4,205,952 | 6/1980 | Cais | 23/230 |
| 4,208,185 | 6/1980 | Sawai et al. | 23/230 |
| 4,208,187 | 6/1980 | Givner | 23/230 |
| 4,230,664 | 10/1980 | Cais | 422/61 |
| 4,233,402 | 11/1980 | Maggio et al. | 435/7 |
| 4,241,176 | 12/1980 | Avrameas et al. | 435/7 |
| 4,246,339 | 1/1981 | Cole et al. | 435/7 |
| 4,270,923 | 6/1981 | Kondo et al. | 23/230 |
| 4,279,617 | 7/1981 | Masson et al. | 23/230 |
| 4,308,026 | 12/1981 | Mochida et al. | 23/230 |
| 4,313,734 | 2/1982 | Leuvering | 23/230 |

(List continued on next page.)

FOREIGN PATENT DOCUMENTS

| | | |
|---|---|---|
| 0254081 | 1/1988 | European Pat. Off. . |
| PCT/US85/-00870 | 3/1985 | PCT Int'l Appl. . |
| PCT/US85/-02534 | 4/1985 | PCT Int'l Appl. . |
| 1341152 | 1/1989 | United Kingdom . |

OTHER PUBLICATIONS

Marc Horisberger and Jacqueline Rosset, "Colloidal Gold, A Useful Marker For Transmission And Scanning Electron Microscopy", *J. Histochem. Cytochem.* vol. 25, 1977, pp. 295-305.

(List continued on next page.)

*Primary Examiner*—Jill A. Johnston
*Attorney, Agent, or Firm*—Staas & Halsey

[57] ABSTRACT

An immunoassay procedure for detection of analytes in urine wherein an immunological reaction is conducted in an aqueous phase containing the urine and a filterable immunocomposite containing an inherently colored gold sol particle is formed if the assay is positive. The colored, gold sol particle containing immunocomposite is collected for direct visual observation on a filter element. False positive readings are minimized by (1) removing contaminants from the urine to prevent clogging of the filter element and non-specific binding of unreacted reactants thereto by contacting the urine with a porous contact element having a detergent material dispersed on its external and interstitial surfaces; (2) preventing non-specific binding of unreacted immunoreactive substances to the filter element by blocking the latter with polyvinyl pyrrolidone; and/or (3) including a green dye material in the aqueous reaction phase to improve the optical distinction after washing the collection filter between negative and positive results on the filter.

90 Claims, 1 Drawing Sheet

U.S. PATENT DOCUMENTS

| | | | |
|---|---|---|---|
| 4,376,110 | 3/1983 | David et al. | 436/513 |
| 4,397,959 | 8/1983 | Hechemy | 436/509 |
| 4,407,943 | 10/1983 | Cole et al. | 435/7 |
| 4,419,453 | 12/1983 | Dorman et al. | 436/534 |
| 4,446,238 | 5/1984 | De Mey et al. | 436/527 |
| 4,468,470 | 8/1984 | Aalberse | 436/539 |
| 4,486,530 | 12/1984 | David et al. | 435/7 |
| 4,552,839 | 11/1985 | Gould et al. | 435/7 |
| 4,557,998 | 10/1985 | Washburn et al. | 430/367 |
| 4,595,661 | 6/1986 | Cragle et al. | 436/534 |
| 4,623,461 | 11/1986 | Hossom et al. | 210/445 |
| 4,628,037 | 12/1986 | Chagnon et al. | 436/526 |
| 4,632,901 | 12/1986 | Valkirs et al. | 435/5 |
| 4,636,479 | 1/1987 | Martin et al. | 436/533 |
| 4,655,814 | 4/1987 | Simpson | 71/67 |
| 4,727,019 | 2/1988 | Valkirs et al. | 435/5 |
| 4,811,866 | 3/1989 | Golias | 222/189 |
| 4,859,612 | 8/1989 | Cole et al. | 436/523 |
| 4,868,131 | 9/1989 | Hiratsuka | 436/528 |
| 4,870,005 | 9/1989 | Akiyoshi et al. | 435/7 |
| 4,880,751 | 11/1989 | Georghegan | 436/518 |

OTHER PUBLICATIONS

P. K. Chun and A. E. Chu, "Colloidal Gold in Immunodot and Immunofiltration Blot Assays for Rapid Serodiagnosis and Direct Specimen Testing", *Abstracts of the Annual Meeting-1986, International Congress of Immunology*, p. 363 (Abstract C-213).

M. Horisberger, Jacqueline Rosset and H. Bauer, "Colloidal Gold Granules as Markers for Cell Surface Receptors in the Scanning Electron Microscope", *Experimentia*, vol. 31, pp. 1147-1149, 15 Oct., 1975.

Malcolm L. Gefter, David H. Margulies and Matthew D. Scharff, "A Simple Method for Polyethylene Glycol-Promoted Hybridization of Mouse Myeloma Cells", *Somatic Cell Genetics*, vol. 3, No. 2, 1977, pp. 231-236.

Marc J. Shulman and Georges Köhler, "Immunoglobulin μ and Heavy Chain Classes are not Determined by Class-Specific RNA-Splicing Enzymes", *Nature*, vol. 274, pp. 917-919, (1978).

N. R. Klinman, A. R. Pickard, N. H. Sigal, P. J. Gearhart, E. S. Metcalf and S. K. Pierce, "Assessing B Cell Diversification by Antigen Receptor and Precursor Cell Analysis", *Ann. Immunol. (Inst. Pasteur)*, vol. 127 C, pp. 489-502 (1976).

S. L. Goodman, G. M. Hodges, L. K. Trejdosiewicz and D. C. Livingston, "Colloidal Gold Markers and Probes for Routine Application in Microscopy", *Journal of Microscopy*, vol. 123, Pt. 2, Aug. 1981, pp. 201-213.

G. Frens, "Controlled Nucleation for the Regulation of the Particle Size in Monodisperse Gold Suspensions", *Nature*, 241, pp. 20-22 (1973).

William D. Geoghegan, and G. Adolph Ackerman, "Adsorption of Horseradish Peroxidase, Ovomucoid and Anti-Immunoglobulin to Colloidal Gold for the Indirect Detection of Concanavalin A, Wheat Germ Agglutinin and Goat Anti-Human Immunoglubulin G on Cell Surfaces at the Electron Microscopic Level: A New Method, Theory and Application", *J. Histochem. Cytochem.*, vol. 25, 1977, pp. 1187-1200.

Millipore Corporation, "Millipore Catalogue and Purchasing Guide", Bedford, Mass. 01730, Sep. 1985.

MZI International, "Micropipetes with Filter", 1 page., date unknown but admitted to be prior art publication.

SOL CAPTURE IMMUNOASSAY KIT AND PROCEDURE

BACKGROUND OF THE INVENTION

1. Field of the Invention

The present invention relates to immunological procedures for determining and/or detecting the presence or amount of an immunologically reactive analyte such as a ligand or ligand receptor in an aqueous phase sample. In particular, the invention relates to improved materials and methodology for detecting the presence of hormonal analytes such as human chorionic gonadotropin (hCG) and/or human luteinizing hormone (hLH) in urine, the presence of such hormonal analytes being indicative of conditions such as pregnancy and of phases in the female menstrual cycle. In another aspect, the invention relates to improved materials and methodology for use in connection with the metal sol capture immunoassay procedures and kits disclosed in co-assigned U.S. application Ser. No. 105,285, filed Oct. 7, 1987 (now U.S. Pat. No. 4,859,612), the entirety of the disclosure of which is hereby specifically incorporated by reference. Additionally, the disclosure of the '285 application provides an excellent description of prior developments in the field of diagnostic procedures based on immunochemistry and reactions.

2. Description of Prior Activities and Developments

In accordance with certain specific procedures disclosed in said '285 application, antibody coated gold sol particles and antibody coated solid phase particles are dispersed in an aqueous system containing human urine. The antibodies are respectively and specifically immunoreactive with respect to different epitopes on a searched for analyte in the urine, and if such analyte is present, the respective antibodies will immunoreact therewith to form a collectible, solid phase, gold particle containing immunocomposite which may then be collected on a filter element mounted in a suitable collection device. Such collection devices are the subject of another co-assigned, U.S. application Ser. No. 107,240, filed Oct. 13, 1987 (now U.S. Pat. No. 4,999,163). The entirety of the disclosure of the '240 application is also specifically incorporated herein by reference. The collected gold sol particle containing composite has a distinctive pink to purplish coloration that is readily visually detected upon observation with the naked eye. The intensity of the coloration of the composition, generally speaking, is directly related to the amount of analyte that is present in the sample.

In the past, false positive readings have sometimes been the result when procedures such as those disclosed in the '285 application were used to test for hCG or hLH. The exact causation for such false readings is not completely understood; however, it is believed that the false positive readings are the result of several separate phenomena. Firstly, human urine contains certain sedimentation which may tend to clog the pores of the collection filter and prevent, or at least inhibit flow of the aqueous reaction phase through the filter. Thus, gold particles carrying antibodies which have not reacted to form an immunocomposite may be prevented from flowing through the filter and as a result will be non-specifically present on the filter even after washing to exhibit the pinkish to purplish coloration that is the inherent characteristic of the gold sol particle. Secondly, collection filter membranes of the type utilized in connection with the present invention sometimes have a tendency to non-specifically bind unreacted antibody so as to retain unreacted gold sol particles on the collection membrane. Thirdly, certain substances in urine may act to increase the tendency of the collection filter element to non-specifically bind unreacted immunoreactive substances. Additionally, the pinkish to purplish environment that surrounds the test materials and reaction phase may provide an optical impression that persists to cause an uncolored collection filter to appear slightly pink to an untrained eye, even after washing, and thus the test may provide a false appearance of being slightly positive or at least an appearance that is confusing.

The presence of contamination in urine has been addressed previously in "Principles of Biochemistry", White, Handler, Smith, Hill Lehman, 6th Edition, McGraw-Hill, at page 1077, where the contaminants are described as consisting of nucleoproteins or microproteins together with some epithelial cells. Such phenomena has also been recognized in U.S. Pat. Nos. 3,873,682 and 4,270,923. However, in none of these prior disclosures is there any mention that such contaminants might interfere with an immunoassay procedure by clogging a collection filter, by enhancing the tendency for the filter to bind non-specifically with immunoreactive substances, or by otherwise interfering with the filtration operation. Rather, in the case of both such prior patents, the urine contaminants caused a turbidity which interfered with the agglutination procedure employed, and in each case a specific solid contact material was used, hopefully to remove the turbidity causing materials without disturbing the analyte content of the urine. However, these and other attempts to remove undesirable impurities from urine samples have sometimes resulted in removal also of the analyte that is to be determined and/or detected, thus foiling the entire procedure.

SUMMARY OF THE INVENTION

The present invention provides relief from the shortcomings described above and generally enhances the immunoassay procedure. In particular the invention minimizes the tendency for false positive observations to be made in connection with procedures and kits wherein a visually detectable reaction product is collected and observed directly visually on a collection element such as a filter. Thus, in an important aspect the present invention relates to a process for the determination and detection of an immunologically reactive analyte in a urine sample, which process includes the steps of (a) providing a labelled component comprising the coupling product of a first immunologically reactive substance and a colored particle, (b) providing a solid phase component comprising the coupling product of a second immunologically reactive substance and a solid phase particle, (c) forming a mixed aqueous suspension of said components and which contains a urine sample to be analyzed for analyte, said substances being capable of binding directly or indirectly as a function of the presence of said analyte to thereby form a filterable, solid phase composite which contains said colored particle, (d) collecting the composite on a filter element and (e) determining or detecting the analyte in the sample by evaluating, through direct visual examination, the presence of said colored particle in the collected composite. In particular the invention provides an improvement of such process which comprises the steps of treating the urine sample to be analyzed for analyte to remove undesirable contaminants therefrom without affecting the analyte content thereof; coating the filter element with a blocking agent effective to reduce non-specific binding of unreacted immunochemically reactive substances; including a sufficient amount of a color forming material in the aqueous suspension to provide the suspension and initially the collected composite with a coloration that is capable of masking the color of the colored particles; and thereafter removing the color of the color forming material from the collected composite. Through the use of the improved process thus described, the flow of aqueous phase media and unreacted components through the filter element and direct visual evaluation of the results of the assay are each facilitated, whereby false positive readings of color on the filter element are minimized.

In accordance with the more specific aspects of the invention, the colored particle may comprise a gold sol particle, and the color forming material may provide the suspension with a green or blue coloration. In accordance with another specific aspect of the invention, the urine sample may be treated to remove undesirable contaminants by contacting the sample with a material having hydrophilic characteristics dispersed on the surface of a porous carrier member. In another more specific aspect of the invention, the blocking agent may comprise polyvinyl pyrrolidone.

In another respect the present invention provides a process for the determination and detection of an immunologically reactive ligand in a urine sample, wherein the process comprises the steps of: providing a labelled component which comprises the coupling product of a first antibody to said ligand and a metal sol particle, said component being of a size and character to enable the same, upon dispersion in an aqueous medium, to form a generally stable suspension of the labelled component; providing a solid phase component which comprises the coupling product of a second antibody to said ligand and a solid phase particle of a size and character to facilitate the maintenance of a generally stable suspension of the solid phase component, said first and second antibodies being different and each being specifically immunoreactive relative to a respective different epitope of said ligand; treating the urine sample to be analyzed for said ligands to selectively remove from the urine contaminants which might interfere with further immunoprocessing and filtration of an aqueous system containing the treated sample; forming a mixed aqueous suspension of said labelled component and said solid phase component and which contains said treated urine sample, said components being capable of being bound together by said ligand to present a filterable solid phase composite that contains said metal sol particle; including in said suspension a sufficient amount of a color forming material to provide said suspension with a coloration that is capable of masking, that is hiding, the inherent coloration of the metal sol particle; allowing the suspension to incubate for a sufficient amount of time for immunoreaction to take place; coating a filter element with a blocking agent effective to reduce non-specific binding of unreacted antibodies thereto; filtering the incubated suspension using the coated filter element to thereby collect the composite on the coated filter element, said filter element and said collected composite initially having a coloration resulting from the presence of the color forming material; and washing the filter element and the collected composite to remove the color forming material and thus expose the inherent color of the filter element and of the metal particle if present, whereby to facilitate flow of aqueous phase media and unreacted components through the filter element and direct visual observation of the inherent color of the metal sol particle in the composite on said filter element.

In one aspect of the invention, the invention provides a process for treating the urine sample to be used in an immunological diagnostic procedure so as to remove undesirable contaminants from the urine without affecting the analyte content thereof. As set forth above, the undesirable components may clog the collection filter and/or may increase the tendency of the filter to bind non-specifically with unreacted immunoreactive substances. In accordance with the invention, the process for treating the urine sample includes the steps of providing a member comprising a solid surface and material dispersed on said surface that is capable of providing the surface with hydrophilic characteristics, and then contacting the urine sample to be treated with the hydrophilic surface of the member. More specifically the member may comprise a porous plug and the surface thereof where the hydrophilic material is dispersed may comprise the external and interstitial surfaces of the porous plug. More particularly, the porous plug may be formed from an ultra high molecular weight polyethylene material and preferably has a nominal pore size of about 10 $\mu$. Preferably the material capable of providing the surface with hydrophilic characteristics may be a detergent or other amphipathic material.

The invention also provides a device for contacting and treating a urine sample to be used in an immunological diagnostic procedure so as to remove undesirable contaminants from the urine without affecting the analyte content thereof. Such device, in accordance with the invention, comprises a contact member having a solid surface and a material dispersed on the surface of the member and capable of providing the surface with hydrophilic characteristics. Preferably the device comprises the porous plug described above which has a detergent material dispersed on its surfaces. In an important but specific aspect of the invention, the device may include a plastic dropper member comprising a bulb and a hollow nozzle and the plug may be mounted in the nozzle of the dropper. Thus, the urine is brought into contact with the surfaces of the plug that are coated with a detergent material by operating the dropper member to first suck urine through the porous plug and into the bulb and then reversing the flow of the urine to expel the treated urine from the dropper back through the plug. In this aspect of the invention it has been found that the hydrophilic characteristics of the coated surfaces provided by the detergent or other amphipathic material also promote the flow of urine through the porous plug.

In another important aspect, the invention relates to an immunological diagnostic procedure wherein an immunological reaction is conducted in an aqueous phase and the results of the reaction are evaluated by visual observation of a colored reaction product collected on a solid collection surface. In accordance with the invention, such procedure is improved by providing the aqueous phase and initially the collected reaction product with a coloration that is capable of masking the inherent color of the collected reaction product. Such procedure provides a sharp and distinctive differential between the color of the reaction system and the color of the reaction product on the collection surface to thereby prevent optical misconceptions created when the reaction system and the reaction product are always of the same color and avoid the temptation and tendency for an untrained observer to see a color on the collection device when there is actually no color there. For example, when the colored reaction product is a solid phase immunocomposite that contains gold sol particles and thus has a generally pink to purplish hue, the aqueous phase may be provided with an essentially complimentary green or a blue or blue green coloration capable of masking the pink to purplish hue of the immunocomposite. When the immunocomposite is collected on the collection surface the coloration thereof becomes intensified so that the same is visible. When the amount of immunocomposite is relatively low, a washing step may preferably be utilized to remove residual green coloration from the filter element and thus completely expose the pink to purplish coloration of the collected reaction product. The change in color in either case is distinct and apparent. On the other hand, if the test is negative and there has been no collection of colored reaction product on the collection surface, upon washing the green coloration away, the surface becomes apparently white and there is no residual visual tendency to see a pink to purplish coloration. If the preferred test procedure includes a washing step, the green coloration may thus provide a control which informs the user that the wash step has not yet been performed.

In conventional procedures, when the reaction media is initially poured through a collection filter, the filter retains a pinkish to purplish coloration because such coloration is contained in the reaction media. Normally the collection surface is then washed and such washing is intended to wash away all color which is not specifically contained in an immunocomposite as a result of a positive test. Thus, the collection surface desirably changes from a pink to purplish coloration to white. However, some human eyes lack the ability to adjust sufficiently rapidly and there is tendency to continue seeing the pink to purplish coloration even when no such coloration remains on the collection surface. This tendency results in false positive observations. On the other hand, when the masking coloration of the present invention is used, as the reaction phase is brought into contact with the collection surface, the latter and any immunocomposite collected thereon take on the coloration of the masking dye. Upon washing, when the test is positive the color of the collection device sharply changes from the color of the mask to the generally pink to purplish coloration of the gold sol particle. On the other hand, when the test is negative, upon washing the coloration of the collection surface sharply changes from the color of the mask to white and there is no tendency to try to continue to see a pink to purplish hue on the collection surface since the eyes of the user have not previously been exposed to the pink to purplish coloration of the positive result.

In another aspect the invention provides an immunological diagnostic kit containing materials for conducting an immunological procedure wherein an immunological reaction is conducted in an aqueous phase and the results of the reaction are evaluated by visual observation of a colored reaction product collected on a solid collection surface. In accordance with the invention, the kit includes, as a component thereof, an amount of a color forming material to be included in the aqueous phase during the reaction, said color forming material being capable of providing the aqueous phase with a coloration which masks the inherent color of the reaction product. Preferably the color forming material should also be capable upon contacting the collection surface of initially providing the collection surface and the collected reaction product thereon with the coloration of the color forming material, and of being rinsed away from the surface of the filter and the collected product to unmask and expose the inherent color of the collection surface and of the collected immunocomposite for visual observation.

The invention also provides a method and means for preventing non-specific binding of unreacted immunologically reactive materials to the collection surface which comprises coating the latter with a blocking agent. Preferably the blocking agent comprises polyvinyl pyrrolidone.

DETAILED DESCRIPTION OF PREFERRED EMBODIMENTS

In accordance with the present invention, a process is provided for determining and detecting immunological reactive analytes, particularly in urine samples. In particular the invention provides improvements for the procedures, materials and kits described in U.S. Pat. No. 4,859,612 referred to above. The invention also provides methodology and a device for treating urine samples to be used in an immunological diagnostic procedure so as to remove undesirable contaminants from the urine without affecting the analyte content thereof. Additionally, the invention provides procedures and kits wherein the visualization of the assay results is improved by means of an optical effect. Further, the invention provides a procedure and means whereby the visualization of the test results on a collection filter is improved by minimizing non-specific binding of unreacted substances to the collection filter.

In a preferred commercial usage of the invention, the same is applicable to assay formats IV(f) and (g) described in U.S. Pat. No. 4,859,285. On the other hand, the invention has more universal application, and might in fact be utilized (1) where urine samples need to be treated for removal of undesirable contaminants without effecting analyte content, (2) where colored reaction products are collected on solid surfaces for direct visual observation and/or (3) where it is desirable to prevent nonspecific binding of unreacted immunologically reactive materials to a surface where reacted materials are collected for evaluation of assay results.

In accordance with the present invention, procedures, kits and materials are provided for determining pregnancy by detecting the presence of hCG in urine and for determining critical phases in the menstrual cycle by detecting the presence of hLH in urine. The present invention is particularly applicable to home diagnostic test kits for use by untrained persons. In the simplest form of the present invention, urine is treated for removal of undesirable contaminants and is mixed with test chemicals which include a distinctively colored dye material. After approximately 5 minutes the mixture, which is the color of the dye material, is poured onto the surface of a filter element which is a part of a device which promotes flow of liquid through the filter. Initially the surface of the filter is the color of the dye material, but upon rinsing the color of the dye material disappears, whereupon, if the test is positive the filter element will have a distinctive pink coloration, and if the test is negative the filter element will be distinctively white.

The procedure for the pregnancy test is based upon the principle that when conception has occurred, the human body begins to produce hCG, the pregnancy hormone. hCG is absorbed into the blood, and is responsible for stopping the menstrual cycle. hCG also passe into the urine, where its presence is most easily detected. The procedures to which the present invention particularly apply provide a colored result, most usually a pink coloration, if hCG is present in the urine. The longer the subject has been pregnant, the darker the color will be because there is more hCG present in the urine.

If the test results are negative, no hCG has been detected in the urine indicating that the subject probably is not pregnant.

Identical test procedures may be utilized for detecting the sudden surge of luteinizing hormone (a fertility hormone) that indicates, ovulation should occur within a short period of time, generally about 12 to 24 hours. Using such test, a person is in a position to predict the time period that she is most able to become pregnant, thus providing time to plan and maximize chances of conception.

Desirably, kits designed for home use by untrained persons should be rapid and reliable. In particular such kits should minimize the possibility of the user making false readings of the test results. The present invention is particularly directed to minimizing false readings in assay procedures.

In accordance with the procedures of Examples IV(f) and (g) of said '285 application, the reaction mixture is poured onto a collection matrix. Theoretically, if the assay is positive, the matrix will achieve a pink coloration, whereas if the test is negative the color of the capture matrix will remain unchanged, usually white. False positive readings of the color on the collection matrix may result from a number of phenomena; however, it is believed that the principal reasons for false readings are slow flow of the reaction mixture through the filter, non-specific binding of otherwise unreacted immunoreactive materials to the collection substrate, and the inherent subjective nature of optical perceptions. With regard to the first two phenomena, it is pointed out that in accordance with the assay procedures of Examples IV(f) and (g) of the '285 application, small gold sol particles with antibodies attached and latex particles with antibodies attached are brought into contact with a urine sample. If the searched for analyte is present, the latex particles and the gold sol particles become joined together through the antigen to thus form an immunocomposite which is large enough to be filtered from the reaction mixture.

Upon collection of the immunocomposite, its inherent coloration due to the presence of the gold sol particles therein becomes concentrated on the collection surface to there provide a pink to purplish coloration. If there is no analyte in the urine sample, such composites are not formed and the inherently colored gold sol particles remain so small that they theoretically cannot be captured by the capture filter element. However, if the flow through the filter element is impeded, the otherwise mobile gold sol particle might be unable to flow through the filter. Thus, the inherent coloration of the gold sol particles will appear on the capture element even though no immunocomposite has been formed. Also, there is a possibility that unreacted antibodies on the gold sol particles might non-specifically bind to the surface of the collection element. In this latter regard, the undesirable contaminants in urine may include components which stick to the filter element and/or alter its properties so as to increase the tendency of the filter element to bind non-specifically with unreacted immunoreactive substances. In either case, slow flow of liquids through the collection filter or non-specific binding of antibodies to the filter element, false positive readings are the result.

Another source of false positive reading of the results of such an assay might be considered to be the result of optical misconceptions and false impressions. Ordinarily the reaction mixture has a pink coloration which is the result of the gold sol particles in the reaction mixture. Whether or not the subject analyte is present in the reaction mixture, the reaction phase mixture generally has a coloration resulting from the gold sol particles. When the mixture is then poured onto the capture media, the latter becomes at least slightly colored by the reaction phase, whether or not the test is positive. A rinse step is typically utilized to rid the capture element of non-specifically bound materials; however, the eye is not always responsive to the elimination of coloration from the collection element. That is to say, there is a tendency for the human observer to have his or her observation capabilities hindered by memory of the pink coloration. It is sometimes difficult to clear the mind of the pink coloration so as to be sure that the pink coloration has been removed upon washing. The present invention provides a method and materials for eliminating the false positive impression by masking or hiding the inherent coloration of the colored particles in the test system by incorporating a dye material in the test system to thus improve the optical distinction between negative and positive readings.

In accordance with the preferred form of the invention, which provides a test procedure for detecting the presence of hCG in the urine at levels of about 50 mIU/ml or greater, it has been found that the color green may be used to mask the inherent pink coloration of the gold sol particles. Blue has also been used to mask the gold sol coloration, particularly in tests for hLH. The selection of the color and quantity of the masking material to be used for a given situation must simply be made somewhat empirically using the criteria that the color of the color forming material and the concentration thereof should be sufficient to provide the test system and initially the collection element and the collected immunocomposite with a coloration that completely hides or masks the color of the colored particle. The amount of the colored masking material to be used in a given test is dependent upon the intensity of the coloration of the colored labelled component in the reaction system. More intense coloration of the colored labelled component requires a greater amount of masking material to effect the mask. Suffice it to say that the whole idea is to eliminate the coloration that is characteristic of a positive result from the environment of the test prior to the visual evaluation of the test result. Thus, the color provided by the masking material should be distinctively and sharply different from the coloration provided by the labelled component, and preferably, although not necessarily, may be generally complimentary thereto.

To improve the flow of materials through the collection filter element and/or minimize non-specific binding of immunoreactive substances thereto, the invention provides for the treatment of the urine sample to remove undesirable contaminants therefrom without affecting the analyte content of the sample. In accordance with a preferred form of the invention, the urine is brought into contact with surfaces of a porous carrier member that are coated with a material capable of increasing the hydrophilicity of the carrier member surfaces, the latter generally initially being hydrophobic in character. A porous member is preferred, in accordance with the present invention, to maximize the contact surface available in a small volume.

Figure 1:
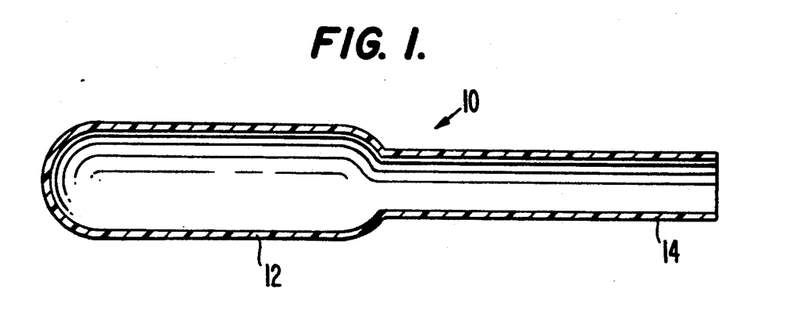
FIG. 1 is a cross-sectional view of a dropper member useful in accordance with the principles and concepts of the present invention.
Figure 2:
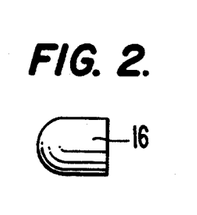
FIG. 2 is a view of a porous plug used in conjunction with the dropper member of FIG. 1.
Figure 3:
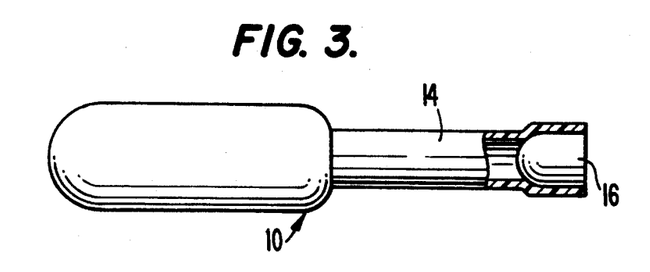
FIG. 3 is a cross-sectional view of an assembled device consisting of the dropper member of FIG. 1 and the porous plug of FIG. 2.

A particularly effective device for treatment of urine to remove certain undesirable materials therefrom is illustrated in FIGS. 1 through 3 of the drawings. The illustrated device comprises a one piece, preferably blow molded, polyethylene body 10, comprising a flexible bulb 12 at one end and an elongated, cylindrical housing or nozzle 14 at the other end. The device 10 does not need to be very large because it is to deal with relatively small quantities of materials, and the same is designed to be discarded after use. A commercially valuable form of the dropper device might be approximately 2¾ inches long, with a flexible bulb 12 that is ½ inch in diameter and with a nozzle 14 that is approximately ¼ inch in diameter. The device might have a wall thickness that is approximately 0.023 inches in thickness. The wall thickness of the dropper may be varied for purposes of adjusting the flux or fill time of the dropper. Desirably the filter dropper should fill with urine in about 3 seconds. The flux time may be varied by adjusting the physical properties of the dropper, including the pore size and void volume of the filter member and the hydrophilicity of the latter provided by the coating material. A tight fit between the plug and the internal diameter of the nozzle 14 is desirable to avoid bypass and thus the force fit of the plug into the nozzle is an important factor.

A porous, ultra high molecular weight polyethylene plug 16, having an outer diameter slightly larger than th initial inner diameter of nozzle 14, is forced into the latter as illustrated in FIG. 3, where it can be seen that the plug 16 causes distension of nozzle 14 and creates a frictional fit to hold plug 16 in place during operation.

Plug 16, which may have a nominal pore size in the range of from about 10 μ to about 35 μ, and preferably of about 10 μ, may preferably be constructed of an ultra high molecular weight polyethylene material that is essentially hydrophobic in character. In accordance with the invention, the external and interstitial surfaces of the plug material are coated with a material to increase the hydrophilicity of the surfaces of the plug.

A porous material which has been found to be useful in connection with the construction of plug 16 is available commercially from Porex Technologies of Fairburn, Ga. The material, known as LABPOR, is available in cylindrical portions having a diameter of approximately 0.25 inch and a length of approximately 0.34 inch, all as illustrated in FIG. 2. The inner diameter of nozzle 14 may be adjusted to a value slightly less than the diameter of the rod to provide a snug frictional fit when the plug 16 is initially forced into the nozzle 14. The ultra high molecular weight polyethylene porous plug material is available from Porex in a variety of pore sizes, void volumes and material hardnesses. These parameters may be varied to provide the desired process characteristics. Moreover, other porous materials having a large surface area to volume ratio should be useful in connection with the invention. The major criteria simply being to provide a device having surface areas which may be coated with a material which provides hydrophilic characteristics so that the device is able to effectively remove undesirable contaminants from the urine without disturbing the analyte content thereof, while at the same time facilitating reasonably rapid flow of urine through the treatment device.

As set forth above, the important purpose of the urine treatment device is to remove particulate contaminants from the urine so as to enhance the flow of the assay liquid phase through the filter element and minimize non-specific binding in situations where assay results are to be visually evaluated. An important criteria in the selection of the porous plug, then, is to select a treatment device which removes undesirable contaminants from the urine so that the collection filter remains unclogged and non-specific binding is diminished and the test sample is able to flow through the collection filter element in a period less than about 1 minute or so.

In accordance with the invention, the interstitial and external surfaces of the porous plug are coated with a material capable of improving the overall hydrophilicity of the plug surfaces and enable the plug to more efficiently remove undesirable contaminants from the urine, but without affecting the analyte content. As discussed above, the problem of contamination of urine is known, for example, from U.S. Pat. No. 3,873,682 and 4,270,923. These prior patent disclosures both address the problem by relying on the chemical characteristics of the fibrous material itself to attract and remove contaminants from urine. In the present case, however, the surfaces, including the interstitial surfaces, of the porous plug are coated with a material capable of providing the plug surfaces with hydrophilic characteristics which operate to facilitate retention of undesirable contaminants within the interstices of the plug, promote flow of fluid through the plug and prevent adherence of analyte to the coated surfaces.

In the broadest aspects of the invention, the coating material should be one which is capable of staying in place on the surfaces of the plug and of providing such surfaces with hydrophilic characteristics. Suitable materials are materials with hydrophilic characteristics such as detergents, proteins and peptides, including BSA, and polymers having hydrophilicly active sites along the chain. Preferably the material may be amphipathic with hydrophobic characteristics to achieve adhesion to the surfaces and hydrophilic characteristics to perform the contaminant removing function in accordance with the invention. A particularly desirable material capable of providing the desired hydrophilic and hydrophobic characteristics comprises polyethylene glycol p-isooctylphenyl ether, a detergent material which is available commercially and is sold under the trade names Igepal CA 630, Antarox A-200, Triton X and Nonidet P-40. Other useful detergents include Tween-20, a detergent comprising polyethoxide units, and sodium dodecyl sulfate. The hydrophilic material may preferably be dispersed on the external and interstitial surfaces of the porous plug by simply immersing such plugs in a solution containing the material having hydrophilic characteristics. In the case of the preferred detergent, the plugs may be immersed in a solution containing about 2.0 grams of Nonidet P-40 in 2.0 liters of 2-propanol. An immersion time of about 15 minutes should suffice for the amphipathic material to effectively be absorbed onto the surfaces of each plug.

It is also possible to remove undesirable contaminants from urine utilizing simple filtration. Both surface filtration and depth filtration have been utilized with some measure of success. When depth filtration is utilized, filtered material is occluded within the filter element as suggested by Goldberg in U.S. Pat. No. 3,862,030, column 2, lines 13-18. When such depth filters are utilized in connection with the present methodology, reliance is made on the fact that it is difficult, if not impossible, to dislodge the filtered material from the filter during reverse flow of the urine, and thus, when a device such as the dropper device 10 utilizes a depth filter instead of the plug 16, the urine is filtered as it is sucked into the device, and then when it is pushed back out the occluded, filtered material cannot be removed from the filter by such back-flushing. Accordingly, the undesirable material may effectively be removed from the urine.

When surface filtration is utilized, the filtered materials which are desirably removed are not occluded deep within the filter. Accordingly, another procedure has been proposed so as to enable the use of surface filters. The undesirable materials are filtered and remain on the outside of the filter during the movement of the urine into the bulb. Then, before the filtered urine is utilized in a test procedure, several drops may be pushed back through the filter to back-flush the same and remove the undesirable materials from the external surface of the filter. The thusly cleaned filter surface permits expulsion of the remainder of the filtered urine from within the device. In a device of essentially the dimensions of the device described above, and utilizing commercially available surface filter elements or materials such a diatomaceous earth, the discarding of three drops has generally proven sufficient to effectively eliminate the undesirable material from the surface of the filter.

In connection with the present invention, the use of a small, integrated unit, such as the dropper device 10 illustrated in the drawings, is necessary for purposes of the overall economics of the procedure and test kits employing such procedure. In this regard, such kits are designed for home use by technically untrained people and it is desirable to employ a small dropper unit which is suitable for a single use and can then be discarded. 2-way flow of the urine through the plug is also desirable for purposes of holding down the cost of the device. 2-way flow necessitates the use of (1) back-flushing to eliminate undesirable materials by discarding the first several drops, (2) a depth filter which occludes the filtered material and eliminates the necessity for back-flushing, as suggested by Goldberg in the '030 patent and/or (3) use, in accordance with the preferred aspects of the present invention, of a treatment surface coated with a material which provides hydrophilic properties for effectively removing undesirable contaminants from the urine sample.

Another factor that improves the overall performance of the porous plug member 16 of the present invention is the fact that the same is wedged tightly into the nozzle 14 of the filter device 10 so as to form a tight frictional fit between the inside of the nozzle and the outer periphery of the porous plug, as is illustrated in FIG. 3. As a result, bypass of fluid material, either during the intake step or the expulsion step, is minimized.

When the preferred form of the invention is utilized, that is, when the device as described in the drawings is utilized and the porous plug element 16 comprises a porous ultra high molecular weight polyethylene plug and the same is coated with Nonidet P-40 detergent and the plug is wedged into the end the nozzle as illustrated, extremely good results are obtained and clogging of the capture filter element and non-specific binding of immunoreactive substances thereto are essentially completely eliminated.

Figure 4:
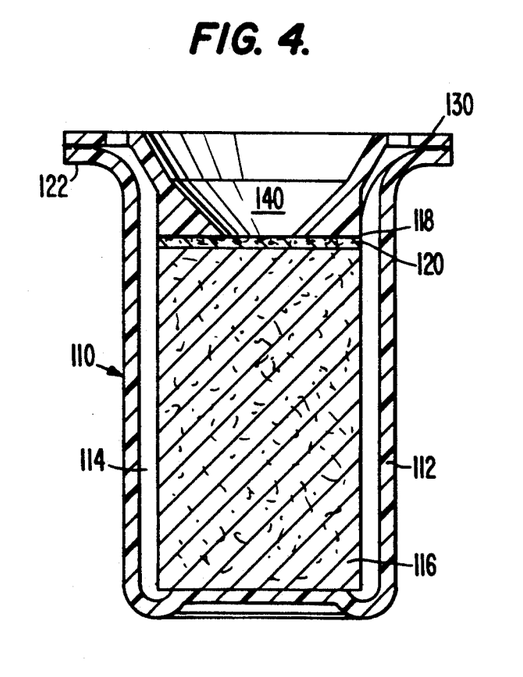
FIG. 4 is a cross-sectional view of a collection device useful in accordance with the invention.

A capture device of the sort described in detail in U.S. Pat. No. 4,999,163 may preferably be utilized in accordance with the preferred form of the present invention. Such device is illustrated in FIG. 4 where it is designated by the reference numeral 110. Device 110 comprises a cup member 112 encompassing a chamber 114 for receiving liquid residues from an immunoassay procedure. An absorbent plug 116 is located in the chamber 114 for promoting flow of liquid into the chamber. A separator 120 is positioned atop plug 116 and a capture element 118 is positioned on separator 120. The capture element 118 is held in place by a lid element 130 which may be welded to the annular upper flange 122 of cup member 112 and provides a funnel shaped throat 140 for directing fluid onto the surface of the capture element 118 and concentrating the captured immunocomposite. The device is described in greater detail in said '240 application and further description is not necessary here. Suffice it to say that for purposes of the present invention, a preferred capture element 118 is made up of borosilicate glass microfibers bound together with an resin binder. Such filter elements are available commercially. A particularly preferred commercially available filter element is the Millipore, type AP-25 filter. The preferred filters are depth filters and the selection of the same must generally be made empirically, considering both retention efficiency and flow characteristics, considerations which must be balanced in order to achieve optimum results. Needless to say, for purposes of the present invention, the filter must have an appropriate retention efficiency to retain the composite materials formed through the immunoreaction which occurs when the unknown analyte is present in the test solution. On the other hand, the flow characteristics of the filter must be such that the liquid reaction media is able to flow through the filter in a short period of time, preferably 1 minute or less, when the filter is in an unclogged condition.

In a particularly preferred form of the invention, the borosilicate microfiber glass filter element may be treated with a blocking agent effective to reduce non-specific binding thereto of unreacted immunologically reactive substances. In particular, the filter element should be treated with a blocking agent sufficient to prevent non-specific binding thereto of the antibodies utilized in accordance with the preferred form of the invention, that is, the antibodies used for detecting the presence of hCG or hLH. A particularly useful blocking agent for purposes of the present invention is polyvinyl pyrrolidone (PVP). Such treated filter elements may be prepared by contacting the filter element, either before or after sizing, with an aqueous immersion solution comprising PVP K-90 at a concentration of about 10 grams PVP per liter of solution.

The capture filter element thus prepared is utilized in accordance with the present invention as the element 118 of device 110 for capturing and collecting the immunocomposite formed in the course of the assay of the invention.

As set forth above, in the particularly preferred form of the invention, the same is utilized for detecting the presence of hCG using assay procedures which are generally the same as those that are described in Examples IV(f) and (g) of said co-pending '285 application. The antibody coated gold sol particles may be prepared essentially as set forth in the prior application and preferably the gold sol particles should have a diameter of approximately 30 nm. (See G. Frens, *Nature*, 241, 20–22 (1973)). The preferred antibody for coating the gold sol particles is the 2G9 antibody described in said prior '285 application. The antibody coated gold sol particles may be processed as set forth in the '285 application to produce a final product, which comprises a suspension of the gold labelled probe particles which may then be used as the labelled component in the preferred immunoassay of the invention. Thus, the labelled component comprises the 2G9 antibody (an immunologically reactive substance) conjugated to an appropriate amount of 30 nm gold sol particles (a colored particle). The 2G9 gold probe suspension may be filtered, assayed and stored using conventional techniques. For storage purposes, the 2G9 gold probe particles may be stored as a suspension in a storage buffer or lyophilized and stored as a freeze dried solid.

In the preferred form of the invention, the assay procedure further involves the use of a solid phase component which comprises the coupling product of a second immunologically reactive substance and a solid phase particle. In this regard, it is to be noted that the preferred assay involves a sandwich reaction wherein the gold probe includes a first antibody to hCG, referred to above as 2G9 antibody. The sandwich assay also involves the use of a second antibody to hCG, which is referred to as 2B2 antibody and described in said '285 application. Manifestly, the 2B2 antibody and the 2G9 antibody are specifically immunoreactive with respect to different sites or epitopes on the hCG molecule. That is to say, 2B2 antibody reacts with the hCG molecule at 1 specific epitopic site, while the 2G9 antibody reacts with the hCG molecule at a different, spatially removed specific epitopic site. Thus, when the test is positive, a composite made up of the gold sol particle, the 2G9 antibody, the hCG molecule, the 2B2 antibody and the latex particle is formed. Such composite is sufficiently large to be captured on a filter element where the inherent and distinctive coloration of the gold probe particles may be visually observed.

Although the present invention is described as pertaining to sandwich assays, it is to be understood that the invention is broader in scope and has application also in connection with competitive and/or inhibition type assays, for example, where the immunologically reactive substance coupled to the colored particle is specifically reactive relative to the immunologically reactive substance coupled to the solid phase particle. Thus, the composite containing the colored particle is formed by direct specific reaction between the first and second substances.

A 2B2 antibody/latex particle probe for use in connection with the preferred form of the invention, may be prepared using any of the various methods and materials disclosed and described in said co-pending '285 application. Moreover, the invention is not limited to the use of latex and there are numerous other solid phase particles known to those skilled in the art which might be used with equivalent results. Many such solid phase particles are described in said '285 application.

In accordance with the preferred embodiment of the present invention, the 2B2 antibody/latex probe particles are prepared by conjugating the 2B2 antibody to 0.99 $\mu$ carboxylated modified latex particles (Polysciences). A 2B2 antibody/latex conjugate suspension is processed using known methodology so that the final product contains the 2B2 antibody carried by an appropriate amount of the 0.99 $\mu$ carboxylated modified latex particles. For storage purposes, the 2B2 antibody/latex probe particles may be stored as a suspension in a storage buffer or lyophilized and stored as a freeze dried solid.

In a preferred form of the invention, an admixture of freeze dried latex probe particles and freeze dried gold sol probe particles may be provided in a single test container (or vial) containing an amount of each probe needed for conducting a single test. The admixture of freeze dried particle may be prepared by forming a single dispersion containing both species of particles and freeze drying the particles together. This provides a simplified kit for commercial purposes. Additionally, other ingredients to be included in accordance with the invention, such as, for example, the color forming material, may be incorporated in the test container at this time. To this end, in accordance with a preferred form of the invention, a green food color dye material may be incorporated as an ingredient in one or both probes prior to freeze drying or may be simply added to the test kit mixture after freeze drying.

Each individual test should preferably contain gold probe particles consisting of about 2.75 $\mu$g of 2B2 antibody conjugated to about 0.27 OD$_{533nm}$ units of 30 nm gold sol particles, latex probe particles consisting of about 6.0 $\mu$g of 2G9 antibody conjugated to about 1.0 OD$_{500nm}$ units of 0.99 $\mu$ carboxylated modified latex particles, and about 6.9 $\mu$g of the green food color dye material. Thus, each test contains a ratio of about 25.6 $\mu$g of the dye for each OD$_{533nm}$ unit of gold sol particle.

The solid green dye that is used in the preferred form of the invention comprises a mixture of FD&C #1 blue and FD&C #5 yellow and the same is commercially available from McCormick and Co., Inc., Baltimore, Md. A 2.5% solution of the green dye corresponds to the liquid green food coloring available at supermarkets.

The test is conducted with urine which has been treated utilizing the treatment device illustrated in the drawings and described above. Accordingly, undesirable, potentially contaminating materials have been removed from the urine. 0.4 milliliters of the treated urine are added to the container which contains a lyophilized powder that includes gold probe particles, the latex probe particles and an the ingredient for producing the green color in the test solution. The vial is swirled gently for 5 seconds and after waiting 5 minutes the contents one or both probes prior to freeze drying or may be simply added to the test kit mixture after freeze drying.

Each individual test should preferably contain gold probe particles consisting of about 2.75 μg of 2G9 antibody conjugated to about 0.27 $OD_{533nm}$ units of 30 nm gold sol particles, latex probe particles consisting of about 6.0 μg of 2B2 antibody conjugated to about 1.0 $OD_{500nm}$ units of 0.99 μ carboxylated modified latex particles, and about 6.9 μg of the green food color dye material. Thus, each test contains a ratio of about 25.6 μg of the dye for each $OD_{533nm}$ unit of gold sol particle.

The solid green dye that is used in the preferred form of the invention comprises a mixture of FD&C #1 blue and FD&C #5 yellow and the same is commercially available from McCormick and Co., Inc., Baltimore, Md. A 2.5% solution of the green dye corresponds to the liquid green food coloring available at supermarkets.

The test is conducted with urine which has been treated utilizing the treatment device illustrated in the drawings and described above. Accordingly, undesirable, potentially contaminating materials have been removed from the urine. 0.4 milliliters of the treated urine are added to the container which contains a lyophilized powder that includes the gold probe particles, the latex probe particles and an ingredient for producing the green color in the test solution. The vial is swirled gently for 5 seconds and after waiting 5 minutes the contents of the test vial are poured through the throat 140 and onto the upper surface of the collecting filter element 118 of the capture device 110 described above. The collection element 118, as set forth above, preferably comprises a polyvinyl pyrrolidone treated borosilicate microfiber glass depth filter. After the throat area 140 of the test well has drained completely, a green coloration remains on collection filter 118 as a result of the green food dye in the reaction mixture. The collection filter 118 may then be then washed by pouring distilled water or a phosphate buffered wash solution through throat 140. After the throat 140 of the washed test well has drained completely, the green coloration will have disappeared and a pink coloration of the surface of the filter element 118 indicates that the subject is pregnant, while a white collection surface indicates the absence of pregnancy.

An identical test procedure was conducted without the dye and it was determined that the average observer had much more difficulty in correctly interpreting the test results, particularly during the early stages of pregnancy when the pink coloration indicating a positive result is necessarily faint. Manifestly, the distinct color change on the collection filter from the green color of the dye to the complimentary pink or purplish tinge of the immunocomposite or alternatively to the white of the filter element generally assists viewers in interpreting the test results.

We claim:

1. In a process for the determination and detection of an immunologically reactive analyte in a urine sample, which process includes the steps of (a) providing a labelled component comprising the coupling product of a first immunologically reactive substance and a colored particle of a first color, (b) providing a solid phase component comprising the coupling product of a second immunologically reactive substance and a solid phase particle, (c) forming a mixed aqueous suspension of said components and which contains a urine sample to be analyzed for analyte, said substances being capable of binding directly or indirectly as a function of the presence of said analyte to thereby form a filterable, solid phase composite which contains said colored component, (d) collecting the composite on a filter element and (e) determining or detecting the analyte in the sample by evaluating, through direct visual examination, the presence of said colored component in the collected composite, the improvement of such process which comprises:
   treating the urine sample to be analyzed for analyte to remove undesirable contaminants therefrom without affecting the analyte content thereof;
   coating said filter element with a blocking agent effective to reduce non-specific binding of unreacted immunologically reactive substances thereto;
   including a sufficient amount of a color forming material of a second color in said aqueous suspension to provide the suspension and initially the filter element and the collected composite with the second color that is capable of masking the first color of the colored particle; and
   thereafter removing the second color of the color forming material from the filter element and the collected composite to expose the inherent color of the filter element or the first color of the colored particle if present,
   whereby flow of aqueous phase media and unreacted components through the filter element and direct visual evaluation of the results of the assay are facilitated and false positive readings of the first color on said filter element are minimized.

2. In a process as set forth in claim 1, wherein said colored particle comprises a gold sol particle.

3. In a process as set forth in claim 2, wherein said color forming material provides the suspension with a green coloration.

4. In a process as set forth in claim 1, wherein said treating the urine sample comprises contacting said sample with a material having hydrophilic characteristics dispersed on the surfaces of a porous carrier member.

5. In a process as set forth in claim 1, wherein said blocking agent comprises polyvinyl pyrrolidone.

6. In a process as set forth in claim 1, wherein said treating the urine sample comprises filtration of the same using a porous filter member.

7. In a process as set forth in claim 6, wherein said filtration comprises surface filtration.

8. In a process as set forth in claim 7, wherein said surface filtration is conducted in a dropper filter device employing forward and reverse flow of the urine through said filter member, and wherein at the initiation of the reverse flow through the filter member, a sufficient number of drops to clean the filter member of undesirable material are discarded.

9. A process for the determination and detection of an immunologically reactive ligand in a urine sample, said process comprising the steps of:
   providing a labelled component which comprises the coupling product of a first antibody to said ligand and a metal sol particle, said component being of a size and character to enable the same, upon dispersion in an aqueous medium, to form a generally stable suspension of the labelled component;
   providing a solid phase component which comprises the coupling product of a second antibody to said ligand and a solid phase particle of a size and character to facilitate the maintenance of a generally stable suspension of the solid phase component, said first and second antibodies being different and each being specifically immunoreactive relative to a respective different epitope of said ligand;

treating the urine sample to be analyzed for said ligand to selectively remove from the urine contaminants which interfere with further immunoprocessing and filtration of aqueous systems containing the treated sample;

forming a mixed aqueous suspension of said labelled component and said solid phase component and which contains said treated urine sample, said components being capable of being bound together by said ligand to present a filterable, solid phase composite that contains said metal particle;

including in said suspension a sufficient amount of a color forming material to provide said suspension with a coloration that is capable of masking the inherent coloration of the metal particles;

allowing said suspension to incubate for a sufficient amount of time for immunoreaction to take place;

coating a filter element with a blocking agent effective to reduce non-specific binding of unreacted antibodies thereto;

filtering said incubated suspension using said coated filter element to thereby collect said composite on the coated filter element, said filter element and said collected composite having a coloration resulting from the presence of the color forming material; and washing said filter element and said collected composite to remove said color forming material and thus expose the inherent color of said filter element and of the metal particle if present, whereby flow of aqueous phase media and unreacted components through the filter element and direct visual observation of the inherent color of the metal particles in the composite on said filter element are facilitated.

10. A process as set forth in claim 9, wherein said metal particle is a gold sol particle which has a pink to purplish inherent coloration and said color forming material is a blue or green dye.

11. A process as set forth in claim 10, wherein said blocking agent is polyvinyl pyrrolidone.

12. A process as set forth in claim 11, wherein said treating the urine sample comprises contacting said sample with a detergent material dispersed on the surface of a porous carrier member.

13. A process as set forth in claim 12, wherein said carrier member comprises a porous plug mounted in a nozzle of a dropper device.

14. A process as set forth in claim 9, wherein said blocking agent is polyvinyl pyrrolidone.

15. A process as set forth in claim 9, wherein said treating the urine sample comprises contacting said sample with a material having hydrophilic characteristics dispersed on the surfaces of a porous carrier member.

16. A process as set forth in claim 15, wherein said carrier member comprises a porous plug mounted in a nozzle of a dropper device.

17. In an immunological diagnostic procedure wherein is included the steps of conducting an immunological reaction in an aqueous phase and evaluating the results of the reaction by visual observation of a colored reaction product collected on a solid collection surface, the improvement of which procedure comprising providing the aqueous phase with a coloration that is capable of masking the inherent color of said reaction product.

18. The improvement as set forth in claim 17, wherein said colored reaction product is a solid phase immunocomposite containing gold sol particles and having a generally pink to purplish hue, and said aqueous phase is provided with a generally green or blue coloration.

19. The improvement as set forth in claim 17, wherein said collection surface comprises the surface of a filter element.

20. The improvement as set forth in claim 19, wherein said filter element surface is initially white.

21. The improvement as set forth in claim 17, wherein the collection surface and said collected reaction product take on the coloration of the aqueous phase during the collection of the reaction product, and said improvement further includes the step of washing said coloration away from the collection surface and the collected reaction product to expose the inherent color of the collection surface and of the reaction product is present.

22. The improvement as set forth in claim 21, wherein said colored reaction product is a solid phase immunocomposite containing gold sol particles and having a generally pink to purplish hue, and said aqueous phase being provided with a generally green or blue coloration.

23. An immunological diagnostic kit for conducting an immunological procedure, said kit containing an immunoreactant coupled to a colored label and which is capable of forming a colored reaction product as a result of an immunological reaction conducted in an aqueous phase and a solid collection surface for collecting the colored reaction product so that the results of the reaction may be evaluated by visual observation of the collected colored reaction product, said kit further including as a component thereof, an amount of a color forming material to be included in said aqueous phase during said reaction, said material being capable of providing the aqueous phase with a coloration that masks the inherent color of said reaction product, capable upon contacting said collection surface of initially providing the collection surface and the collected reaction product thereon with the masking coloration of the material, and capable of being rinsed away from the surface and the product to expose the inherent color of the latter for visual observation.

24. A kit as set forth in claim 23, wherein said colored reaction product is a solid phase immunocomposite containing gold sol particles and having a generally pink to purplish hue, and said color forming material is a green or blue dye.

25. In a process for the determination and detection of an immunologically reactive analyte in a urine sample, which process includes the steps of (a) providing a labelled component comprising the coupling product of a first immunologically reactive substance and a colored particle of a first color, (b) providing a solid phase component comprising the coupling product of a second immunologically reactive substance and a solid phase particle, (c) forming a mixed aqueous suspension of said components and which contains a urine sample to be analyzed for analyte, said substances being capable of binding directly or indirectly as a function of the presence of said analyte to thereby form a colored, collectable, solid phase composite which contains said labelled component, (d) collecting the composite on a collection element and (e) determining or detecting the analyte in the sample by evaluating, through direct visual examination, the presence of said colored component in the collected composite, the improvement of such process which comprises:

including a sufficient amount of a color forming material of a second color in said suspension to provide the suspension and initially the collected composite with the second color that is capable of masking the first color of the colored particle; and thereafter removing the second color of the color forming material from the collection element and the collected composite to thus expose the inherent color of the collection element and the first color of the colored particle if present, whereby direct visual evaluation of the results of the assay is facilitated and false positive readings of the first color on said collection element are minimized.

26. In a process as set forth in claim 25, wherein said colored particle comprises a gold sol particle.

27. In a process as set forth in claim 26, wherein said color forming material provides the suspension with a green or blue coloration.

28. A process for the determination and detection of an immunologically reactive ligand in a urine sample, said process comprising the steps of:

providing a labelled component which comprises the coupling product of a first antibody to said ligand and a metal sol particle, said component being of a size and character to enable the same, upon dispersion in an aqueous medium, to form a generally stable suspension of the labelled component;

providing a solid phase component which comprises the coupling product of a second antibody to said ligand and a solid phase particle of a size and character to facilitate the maintenance of a generally stable suspension of the solid phase component, said first antibody and said second antibody being different and each being specifically immunoreactive relative to a respective different epitope of said ligand;

forming a mixed aqueous suspension of said labelled component and said solid phase component and which contains said urine sample, said components being capable of being bound together by said ligand to present a filterable, solid phase composite that contains said metal sol particle;

including in said suspension a sufficient amount of a color forming material to provide said suspension with a coloration that is capable of masking the inherent coloration of the metal sol particle;

allowing said suspension to incubate for a sufficient amount of time for immunoreaction to take place;

filtering said incubated suspension to thereby collect said composite on a filter element, said filter element and said collected composite thereon initially having the coloration resulting from the presence of the color forming material; and washing said filter element and said collected composite to remove said color forming material and expose the inherent coloration of the filter element and of the metal sol particle if present, whereby direct visual observation of the inherent coloration of the metal particles in the composite on said filter element is facilitated.

29. A process as set forth in claim 28, wherein said metal sol particle is a gold sol particle, wherein said inherent coloration of the gold sol particle is pink to purplish, and wherein said color forming material is a green or blue dye.

30. In a process for the determination and detection of an immunologically reactive analyte in a urine sample, which process includes the steps of (a) providing a labelled component comprising the coupling product of a first immunologically reactive substance and a colored particle, (b) providing a solid phase component comprising the coupling product of a second immunologically reactive substance and a solid phase particle, (c) forming a mixed aqueous suspension of said components and which contains a urine sample to be analyzed for analyte, said substances being capable of binding directly or indirectly as a function of the presence of said analyte to thereby form a filterable, solid phase composite which contains said colored component, (d) collecting the composite on a filter element and (e) determining or detecting the analyte in the sample by evaluating, through direct visual examination, the presence of said colored component in the collected composite, the improvement of such process which comprises:

treating the urine sample to be analyzed for analyte to selectively remove undesirable contaminants which interfere with further immunoprocessing and filtration therefrom without affecting the analyte content thereof, whereby flow of aqueous phase media and unreacted components through the filter element is facilitated and thus false positive readings of color on said filter element are minimized.

31. In a process as set forth in claim 30, wherein said treating the urine sample comprises contacting said sample with a material having hydrophilic characteristics dispersed on the surface of a porous carrier member.

32. In a process as set forth in claim 30, wherein said treating the urine sample comprises filtration of the same using a porous filter member.

33. In a process as set forth in claim 32, wherein said filtration comprises surface filtration.

34. In a process as set forth in claim 33, wherein said surface filtration is conducted in a dropper filter device employing flow of the urine sample through said filter element in a first direction followed by flow of the urine sample through the filter element in a reverse direction, and wherein at the initiation of the flow of the urine sample in a reverse direction through the filter member, a sufficient number of drops of the urine sample to clean the filter member of undesirable material are discarded before the urine sample is used in the process.

35. A process for the determination and detection of an immunologically reactive ligand in a urine sample, said process comprising the steps of:

providing a labelled component which comprises the coupling product of a first antibody to said ligand and a metal sol particle, said component being of a size and character to enable the same, upon dispersion in an aqueous medium, to form a generally stable suspension of the labelled component;

providing a solid phase component which comprises the coupling product of a second antibody to said ligand and a solid phase particle of a size and character to facilitate the maintenance of a generally stable suspension of the solid phase component, said first antibody and said second antibody being different and each being specifically immunoreactive relative to a respective different epitope of said ligand;

treating the urine sample to be analyzed for said ligand to selectively remove from the urine contaminants which interfere with further immunoprocessing and filtration of aqueous systems containing the treated sample;

forming a mixed aqueous suspension of said labelled component and said solid phase component and which contains said treated urine sample, said components being capable of being bound together by said ligand to present a filterable, solid phase composite that contains said metal particle;

allowing said suspension to incubate for a sufficient amount of time for immunoreaction to take place; and filtering said incubated suspension to thereby collect said composite on a filter element, whereby flow of aqueous phase media and unreacted components through said filter element and visual observation of the inherent color of the metal particles in the composite on said filter element are facilitated.

36. A process as set forth in claim 35, wherein said treating the urine sample comprises contacting said sample with a material having hydrophilic characteristics dispersed on the surfaces of a porous carrier member.

37. A process as set forth in claim 36, wherein said carrier member comprises a porous plug mounted in a nozzle of a dropper device.

38. A process as set forth in claim 37, wherein said surface of the porous plug comprises its external and internal surfaces.

39. A process as set forth in claim 38, wherein said plug has a nominal pore size in the range of from about 10 to about 35 $\mu$.

40. A process as set forth in claim 38, wherein said porous plug is formed from ultra high molecular weight polyethylene.

41. A process as set forth in claim 40, wherein said plug has a pore size of about 10 $\mu$.

42. A process as set forth in claim 40, wherein said plug has a nominal pore size in the range of from about 10 to about 35 $\mu$.

43. A process as set forth in claim 42, wherein said material having hydrophilic characteristics comprises an amphipathic material.

44. A process as set forth in claim 43, wherein said amphipathic material comprises a detergent.

45. A process as set forth in claim 44, wherein said detergent comprises polyethylene glycol p-isooctylphenyl ether.

46. In a process for the determination and detection of an immunologically reactive analyte in a urine sample, which process includes the steps of (a) providing a labelled component comprising the coupling product of a first immunologically reactive substance and a colored particle, (b) providing a solid phase component comprising the coupling product of a second immunologically reactive substance and a solid phase particle, (c) forming a mixed aqueous suspension of said components and which contains a urine sample to be analyzed from analyte, said substances being capable of binding directly or indirectly as a function of the presence of said analyte to thereby form a filterable, solid phase composite which contains said colored component, (d) collecting the composite on a filter element and (e) determining or detecting the analyte in the sample by evaluating, through direct visual examination, the presence of said colored component in the collected composite, the improvement of such process which comprises:

treating the urine sample to be analyzed for analyte to selectively remove undesirable contaminants which interfere with further immunoprocessing and filtration therefrom without affecting the analyte content thereof; and coating said filter element with a blocking agent effective to reduce non-specific binding of unreacted immunologically reactive substances thereto, whereby flow of aqueous phase media and unreacted components through the filter element is facilitated and thus false positive readings of color on said filter element are minimized.

47. In a process as set forth in claim 46, wherein said treating the urine sample comprises contacting said sample with a material having hydrophilic characteristics dispersed on the surface of a porous carrier member.

48. In a process as set forth in claim 46, wherein said blocking agent comprises polyvinyl pyrrolidone.

49. In a process as set forth in claim 46, wherein said treating the urine sample comprises filtration of the urine sample using a porous filter member.

50. In a process as set forth in claim 49, wherein said filtration comprises surface filtration.

51. In a process as set forth in claim 50, wherein said surface filtration is conducted in a dropper filter device employing flow of the urine sample through said filter element in a first direction followed by flow of the urine sample through the filter element is a reverse direction, and wherein at the initiation of the flow of the urine sample in a reverse direction through the filter member, a sufficient number of drops of the urine sample to clean the filter member of undesirable material are discarded before the urine sample is used in the process.

52. A process for the determination and detection of an immunologically reactive ligand in a urine sample, said process comprising the steps of:

providing a labelled component which comprises the coupling product of a first antibody to said ligand and a metal sol particle, said component being of a size and character to enable the same, upon dispersion in an aqueous medium, to form a generally stable suspension of the labelled component;

providing a solid phase component which comprises the coupling product of a second antibody to said ligand and a solid phase particle of a size and character to facilitate the maintenance of a generally stable suspension of the solid phase component, said first antibody and said second antibody being different and each being specifically immunoreactive relative to a respective different epitope of said ligand;

treating the urine sample to be analyzed for said ligand to selectively remove from the urine contaminants which interfere with further immunoprocessing and filtration of aqueous systems containing the treated sample;

forming a mixed aqueous suspension of said labelled component and said solid phase component and which contains said treated urine sample, said components being capable of being bound together by said ligand to present a filterable, solid phase composite that contains said metal particle;

allowing said suspension to incubate for a sufficient amount of time for immunoreaction to take place; and coating a filter element with a blocking agent effective to reduce non-specific binding of unreacted antibodies thereto;

filtering said incubated suspension using said coated filter element to thereby collect said composite on the coated filter element, whereby flow of aqueous media and unreacted components through said filter element and direct visual observation of the inherent color of the metal particles in the composite on said filter element are facilitated.

53. A process as set forth in claim 52, wherein said blocking agent is polyvinyl pyrrolidone.

54. A process as set forth in claim 52, wherein said treating the urine sample comprises contacting said sample with a material having hydrophilic characteristics dispersed on the surface of a porous carrier member.

55. A process as set forth in claim 54, wherein said carrier member comprises a porous plug mounted in a nozzle of a dropper device.

56. A process as set forth in claim 54, wherein said surface of said porous plug comprises its external and internal surfaces.

57. A process as set forth in claim 56, wherein said plug has a nominal pore size in the range of from about 10 to about 35μ.

58. A process as set forth in claim 56, wherein said porous plug is formed from ultra high molecular weight polyethylene.

59. A process as set forth in claim 58, wherein said plug has a nominal pore size in the range of from about 10 to about 35 μ.

60. A process as set forth in claim 58, wherein said plug has a pore size of about 10 μ.

61. In a process for the determination and detection of an immunologically reactive analyte in a urine sample, which process includes the steps of (a) providing a labelled component comprising the coupling product of a first immunologically reactive substance and a colored particle of a first color, (b) providing a solid phase component comprising the coupling product of a second immunologically reactive substance and a solid phase particle, (c) forming a mixed aqueous suspension of said components and which contains a urine sample to be analyzed for analyte, said substances being capable of binding directly or indirectly as a function of the presence of said analyte to thereby form a filterable, solid phase composite which contains said colored component, (d) collecting the composite on a filter element and (e) determining or detecting the analyte in the sample by evaluating, through direct visual examination, the presence of said colored component in the collected composite, the improvement of such process which comprises:

treating the urine sample to be analyzed for analyte to remove undesirable contaminants therefrom without affecting the analyte content thereof;

including a sufficient amount of a color forming material of a second color in said aqueous suspension to provide the suspension and initially the filter element and the collected composite with the second color that is capable of masking the first color of the colored particle; and thereafter removing the second color of the color forming material from the filter element and collected composite to expose the first color of the filter element and of the colored particle is present, whereby false positive readings of the first color on said filter element are minimized by facilitating flow of aqueous phase media and unreacted components through the filter element and direct visual evaluation of the results of the assay.

62. In a process as set forth in claim 61, wherein said colored particle comprises a gold sol particle.

63. In a process as set forth in claim 62, wherein said color forming material provides the suspension with a green or blue coloration.

64. In a process as set forth in claim 61, wherein said treating the urine sample comprises contacting said sample with a material having hydrophilic characteristics dispersed on the surface of a porous carrier member.

65. In a process as set forth in claim 61, wherein said treating the urine sample comprises filtration of the urine sample using a porous filter member.

66. In a process as set forth in claim 65, wherein said filtration comprises surface filtration.

67. In a process as set forth in claim 66, wherein said surface filtration is conducted in a dropper filter device employing flow of the urine sample through said filter element in a first direction followed by flow of the urine sample through the filter element in a reverse direction, and wherein at the initiation of the flow of the urine sample in a reverse direction through the filter member, a sufficient number of drops of the urine samples to clean the filter member of undesirable material are discarded before the urine sample is used in the process.

68. A process for the determination and detection of an immunologically reactive ligand in a urine sample, said process comprising the steps of:

providing a labelled component which comprises the coupling product of a first antibody to said ligand and a metal sol particle, said component being of a size and character to enable the same, upon dispersion in an aqueous medium, to form a generally stable suspension of the labelled component;

providing a solid phase component which comprises the coupling product of a second antibody to said ligand and a solid phase particle of a size and character to facilitate the maintenance of a generally stable suspension of the solid phase component, said first and second antibodies being different and each being specifically immunoreactive relative to a respective different epitope of said ligand;

treating the urine sample to be analyzed for said ligand to selectively remove from the urine contaminants which interfere with further immunoprocessing and filtration of aqueous systems containing the treated sample;

forming a mixed aqueous suspension of said labelled component and said solid phase component and which contains said treated urine sample, said components being capable of being bound together by said ligand to present a filterable, solid phase composite that contains said metal particle;

including in said suspension a sufficient amount of a color forming material to provide said suspension with a coloration that is capable of masking the inherent coloration of the metal particle;

allowing said suspension to incubate for a sufficient amount of time for immunoreaction to take place;

filtering said incubated suspension to thereby collect said composite on a filter element, said filter element and said collected composite having coloration resulting from the presence of the color forming material; and washing said filter element and said collected composite to remove said color forming material and expose the inherent color of the filter element and of the metal particle if present, whereby flow of aqueous phase media and unreacted components through said filter element and direct visual observation of the inherent color of metal particles in the composite on said filter element are facilitated.

69. A process as set forth in claim 68, wherein said metal particle is a gold sol particle which has a pink to purplish inherent coloration, and said color forming material is a green or blue dye.

70. A process as set forth in claim 68, wherein said treating the urine sample comprises contacting said sample with a material having hydrophilic characteristics dispersed on the surfaces of a porous carrier member.

71. A process as set forth in claim 70, wherein said carrier member comprises a porous plug mounted in a nozzle of a dropper device.

72. A process as set forth in claim 71, wherein said surface of the porous plug comprises its external and internal surfaces.

73. A process as set forth in claim 72, wherein said plug has a nominal pore size in the range of from about 10 to about 35 $\mu$.

74. A process as set forth in claim 72, wherein said porous plug is formed from ultra high molecular weight polyethylene.

75. A process as set forth in claim 74, wherein said plug has a nominal pore size in the range of from about 10 to about 35 $\mu$.

76. A process as set forth in claim 74, wherein said plug has a pore size of about 10 $\mu$.

77. An immunological diagnostic kit containing materials for conducting an immunological procedure to determine and detect an immunologically reactive analyte in a urine sample and wherein an immunological reactive is conducted in an aqueous phase which contains the urine sample and the results of the assay are evaluated by direct visual observation of a colored reaction product of a first color collected on a surface of a filter element, said kit comprising (1) an amount of a color forming material of a second color to be included in said aqueous phase during said reaction, said material being capable of providing the aqueous phase with a coloration that is able to mask the first color of said reaction product, capable upon contacting said filter element of initially providing the filter element surface and the collected reaction product thereon with the coloration of the color forming material, and capable of being rinsed away from said surface and product to expose the inherent color of said surface and the first color of the reaction product for visual observation; and (2) a device to be used for contacting and treating the urine sample so as to remove undesirable contaminants from the urine without affecting the analyte thereof to thereby facilitate flow of said aqueous phase media through said filter element, said device comprising a contact member having a solid surface and a material having hydrophilic characteristics dispersed on said surface.

78. A kit as set forth in claim 77, wherein said colored reaction product is a solid phase immunocomposite containing gold sol particles and having a generally pink to purplish hue, and said color forming material is a green or blue dye.

79. A kit as set forth in claim 77, wherein said contact member is a porous plug and said surface thereof comprises its external and internal surfaces.

80. A kit as set forth in claim 79, wherein said plug has a nominal pore size in the range of from about 10 to about 35 $\mu$.

81. A kit as set forth in claim 79, wherein said porous plug is formed from an ultra high molecular weight polyethylene.

82. A kit as set forth in claim 81, wherein said plug has a nominal pore size in the range of from about 10 to about 35 $\mu$.

83. A kit as set forth in claim 82, wherein said plug has a pore side of about 10 $\mu$.

84. A kit as set forth in claim 79, wherein said device includes a dropper member comprising a bulb and a hollow nozzle, said plug being disposed in said nozzle.

85. A kit as set forth in claim 84, wherein said plug has a pore size of about 10 $\mu$.

86. A kit as set forth in claim 84, wherein said dropper member is of a one-piece molded construction.

87. A kit as set forth in claim 84, wherein said plug has a nominal pore size in the range of from about 10 to about 35 $\mu$.

88. A kit as set forth in claim 87, wherein said colored reaction product is a solid phase immunocomposite containing gold sol particles and having a generally pink to purplish hue, said color forming material is a green or blue dye, said porous plug is formed from an ultra high molecular weight polyethylene, and said material having hydrophilic characteristics comprises a detergent, and wherein said kit further includes a coating on said filter element comprising a polyvinyl pyrrolidone blocking agent effective to reduce non-specific binding of unreacted immunologically reactive substances.

89. A kit as set forth in claim 77, wherein is included a coating on said filter element comprising a blocking agent effective to reduce non-specific binding thereto of unreacted immunologically reactive substances.

90. A kit as set forth in claim 89, wherein said blocking agent comprises polyvinyl pyrrolidone.

* * * * *